United States Patent
Moeller et al.

(10) Patent No.: US 8,919,371 B2
(45) Date of Patent: Dec. 30, 2014

(54) ROTARY SHEAR INJECTOR VALVE WITH COATED STATOR SURFACE

(75) Inventors: Mark W. Moeller, Kingston, MA (US); Peter Kirby, Derry, NH (US); Theodore D. Ciolkosz, Plymouth, MA (US); Robert A. Jencks, Mendon, MA (US)

(73) Assignee: Waters Technologies Corporation, Milford, MA (US)

( * ) Notice: Subject to any disclaimer, the term of this patent is extended or adjusted under 35 U.S.C. 154(b) by 311 days.

(21) Appl. No.: 13/384,613

(22) PCT Filed: Jul. 23, 2010

(86) PCT No.: PCT/US2010/043004
§ 371 (c)(1),
(2), (4) Date: Jan. 18, 2012

(87) PCT Pub. No.: WO2011/014414
PCT Pub. Date: Feb. 3, 2011

(65) Prior Publication Data
US 2012/0119128 A1 May 17, 2012

Related U.S. Application Data

(60) Provisional application No. 61/229,398, filed on Jul. 29, 2009.

(51) Int. Cl.
*F16K 3/08* (2006.01)
*F16K 25/00* (2006.01)
*G01N 30/20* (2006.01)

(52) U.S. Cl.
CPC .......... *F16K 3/08* (2013.01); *G01N 2030/202* (2013.01); *G01N 30/20* (2013.01); *F16K 25/005* (2013.01)

USPC ................ 137/375; 251/208; 251/368

(58) Field of Classification Search
USPC .................. 251/208, 368; 137/375
See application file for complete search history.

(56) References Cited

U.S. PATENT DOCUMENTS 4,647,494 A    3/1987   Meyerson et al.
4,777,090 A * 10/1988   Ovshinsky et al. ........... 428/408
(Continued)

FOREIGN PATENT DOCUMENTS

JP    62109222    5/1987
JP    06227882    8/1994
(Continued)

OTHER PUBLICATIONS

PCT International Search Report for PCT Application No. PCT/US2010/043004, Form PCT/ISA/220 + 210, mailing date of Sep. 14, 2010, 5 pages.

(Continued)

*Primary Examiner* — John Bastianelli
(74) *Attorney, Agent, or Firm* — Waters Technologies Corporation

(57) ABSTRACT

A valve includes a rotor and a stator. The rotor and the stator each have seal surfaces for contacting and sliding against one another during operation of the valve. Either or both of the rotor and the stator have a seal-surface coating formed by depositing an at least partially amorphous interlayer on a substrate and depositing a surface layer, including diamond-like carbon, on the interlayer. The surface layer requires no mechanical polishing.

13 Claims, 3 Drawing Sheets

(56) References Cited

U.S. PATENT DOCUMENTS

| | | | |
|---|---|---|---|
| 4,837,249 A * | 6/1989 | O'Mara et al. | 427/180 |
| 5,135,808 A | 8/1992 | Kimock et al. | |
| 5,150,737 A * | 9/1992 | Clerc | 251/368 |
| 5,441,776 A * | 8/1995 | Sterling et al. | 428/1.52 |
| 5,643,423 A * | 7/1997 | Kimock et al. | 427/250 |
| 5,829,735 A * | 11/1998 | Ikeda | 251/368 |
| 5,842,097 A * | 11/1998 | Kanbayashi et al. | 428/914 |
| 5,934,321 A * | 8/1999 | Miya et al. | 251/368 |
| 6,080,470 A * | 6/2000 | Dorfman | 428/216 |
| 6,453,946 B2 * | 9/2002 | Nichols et al. | 251/268 |
| 6,517,339 B1 * | 2/2003 | Miya et al. | 425/542 |
| 6,904,935 B2 * | 6/2005 | Welty et al. | 251/368 |
| 7,363,894 B2 * | 4/2008 | Evans et al. | 74/569 |
| 2006/0060811 A1 * | 3/2006 | Kuwata et al. | 251/327 |
| 2006/0257663 A1 * | 11/2006 | Doll et al. | 428/408 |
| 2008/0258094 A1 | 10/2008 | Usowicz et al. | |

FOREIGN PATENT DOCUMENTS

| | | |
|---|---|---|
| JP | 2004028215 | 1/2004 |
| JP | 2004353759 | 12/2004 |
| WO | 9205951 | 4/1992 |
| WO | 9523652 | 9/1995 |

OTHER PUBLICATIONS

PCT International Written Opinion Report for PCT Application No. PCT/US2010/043004, Form PCT/ISA/227, mailing date of Sep. 14, 2010, 5 pages.

Translation of Notice of Rejection for Japanese Patent Application No. 2012-522915, mailing date of Feb. 4, 2014, 3 pages.

* cited by examiner

ROTARY SHEAR INJECTOR VALVE WITH COATED STATOR SURFACE

RELATED APPLICATION

This application claims the benefit of U.S. Provisional Application Ser. No. 61/229,398, filed Jul. 29, 2009, the entirety of which is incorporated herein by reference.

TECHNICAL FIELD

The invention generally relates to valves, and, more particularly, to high-pressure valves that have moving parts and are used in chemical-processing apparatus.

BACKGROUND INFORMATION

The invention relates to valves having moving parts that are subject to loads. Typical fluidic valves have parts that are configured to avoid leakage of fluids. As a valve is cycled between valve states, however, the loads placed on the moving parts cause wear. Loads can be substantial on moving parts, typically a stator and a rotor, of a valve used in analytical instruments. Portions of some analytical instruments operate at high pressure, often requiring application of high pressure at valve-part interfaces. For example, a high performance liquid chromatography (HPLC) pump typically operates at up to 1,000 to 5,000 pounds per square inch (psi); higher pressure chromatography apparatus operate at pressures up to 10,000 psi or greater.

As the pressure of a system increases, the wear on the moving parts of a valve tends to increase and the valve's expected cycle lifetime is reduced. Many valves operating at very high pressures can only withstand 150,000 cycles.

SUMMARY OF THE INVENTION

The invention arises, in part, from the realization that a valve—in a chemical-processing apparatus—having sliding components, can advantageously obtain a substantially smooth diamond-like carbon (DLC) coating on sliding contact surfaces by forming the DLC coating on a substantially smooth interlayer formed of an at least partially amorphous material. The smooth coating provides a good wear rate and friction coefficient, while the use of the amorphous interlayer reduces fabrication complexity and cost in comparison to that of existing valves used in chemical-processing apparatus. Thus, for example, the invention is particularly well suited to provide improved rotary shear injector valves, as used to deliver samples in an HPLC or higher-pressure chromatography apparatus.

Accordingly, one embodiment of the invention features a valve. The valve includes a rotor formed at least in part from a rotor substrate, and a stator formed at least in part from a stator substrate. The rotor and the stator each have seal surfaces; when the valve is assembled and operated, the rotor and stator are in slidable contact at their respective seal surfaces. Either or both of the rotor and the stator have a contact-surface coating formed by depositing an at least partially amorphous or single-crystal interlayer adjacent the respective contact surface, and depositing a surface layer, including diamond-like carbon, on the interlayer. The interlayer provides a substantially smooth layer for growth of a substantially smooth surface layer, which does not require mechanical polishing, in contrast to some prior valves.

A second embodiment of the invention features a method of making the above-described valve.

BRIEF DESCRIPTION OF THE DRAWINGS

The drawings are not necessarily to scale, emphasis instead generally being placed upon illustrating some principles of the invention.

FIG. 2b is a bottom detailed view of a portion of the seal surface of the stator of FIG. 2a;

FIG. 3b is a top detailed view of a central portion of the contact surface of the rotor of FIG. 3a;

DESCRIPTION

For convenience, features of the invention are illustrated, herein, via descriptions of an embodiment of a modified six-port rotary shear injector valve. Multiport injector valves are well known to those of skill in the chromatography arts. In view of the present description, one of skill will recognize that features of the invention are applicable to other types of injector valves, other valves used in chromatography and chemical processing, and, more generally, to other valves and mechanical devices that have components that experience shear surface forces due to sliding motions at component-contact surfaces.

Figure 1:
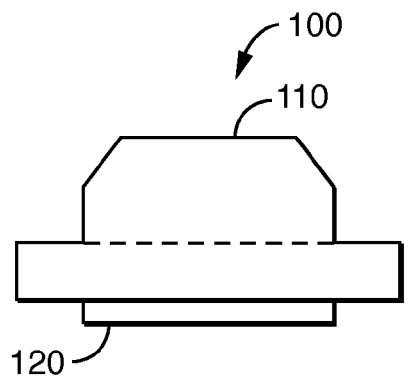
FIG. 1 is a block-diagram side view of a portion of an injector valve, in accordance with one embodiment of the invention.

FIG. 1 is a block diagram of a portion of an injector valve 100, suitable, for example, for HPLC or higher pressure LC, in accordance with one embodiment of the invention. The valve includes a stator 110 and a rotor 120 (other components, which are typical of existing valves, are not shown.) The invention relates to coatings used on sliding contact surfaces of the stator 110 and/or rotor 120. Thus, only the stator 110 and rotor 120 are illustrated and described, for simplicity.

Figure 2A:
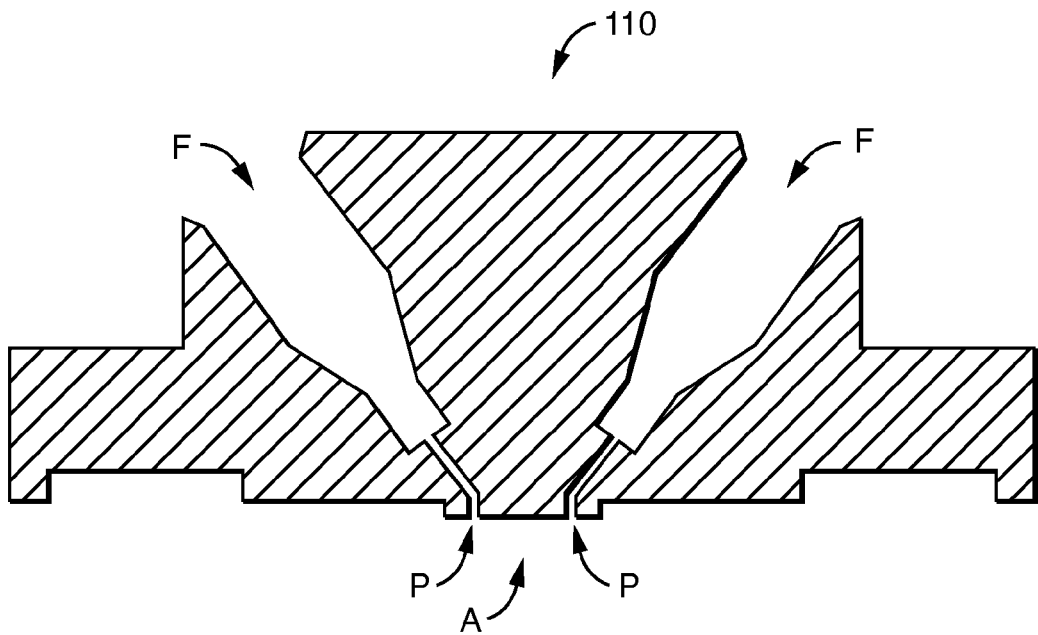
FIG. 2a is a cross-sectional side view of the stator of FIG. 1.

FIG. 2a is a cross section side view of the stator 110. The stator has a seal/contact surface A, which defines six ports that lead to six fittings F (two shown). The fittings F permit tubing connections, as know in the HPLC art, to a solvent pump, a sample source, a sample loop, a waste line, and a separation column.

Figure 2B:
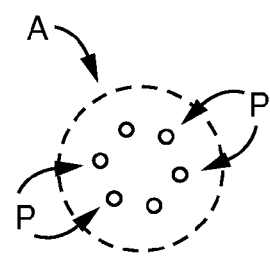

FIG. 2b is a detailed planar view of a portion of the seal surface A of the stator 110. The seal surface A has six ports P (openings), one for each of the six fittings F, as described above. As described in more detail below, the seal surface A of the stator 110 mates with a surface of the rotor 120 that has features that selectably provide fluidic pathways between pairs of the ports P, as desired during operation of the valve 100.

Figure 3A:
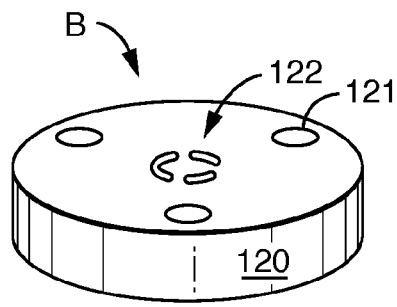
FIG. 3a is a three-dimensional view of the rotor of FIG. 1.

FIG. 3a is a three-dimensional view of the rotor 120. The rotor 120 has three through-holes 121, which engage with a valve shaft (not shown) that, in use, rotates the rotor 120 while pressing the rotor 120 in contact with the stator 110. The rotor 120 also has three grooves 122, defined in a seal/contact surface B, which act as fluid conduits, in cooperation with the seal surface A of the stator 110.

Figure 3B:
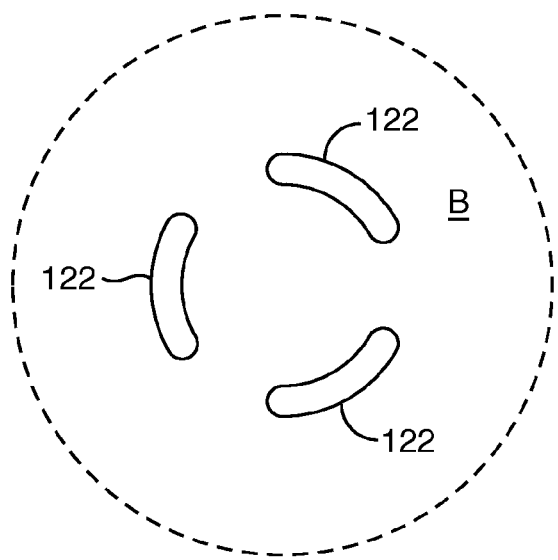

FIG. 3b is a detailed planar view of the central portion of the seal surface B of the rotor 110. When the seal surfaces A, B of the stator 110 and rotor 120 are in contact, the grooves 122 provide fluid conduits that connect pairs of the ports P of the stator 110. By rotation of the rotor 120, against the stator 110, different pairs of ports P are connected for fluidic communication.

Figure 3C:
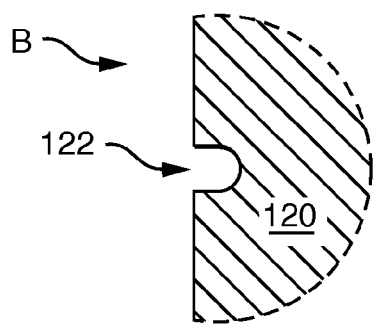
FIG. 3c is a cross-sectional detailed view of the rotor of FIG. 3a, showing a groove in the contact surface.

FIG. 3c is a cross-sectional detailed view of a small portion of the rotor 120, showing the cross-sectional configuration of one of the grooves 122. The depth of the groove 122, in this example, is approximately 200 µm.

Figure 4:
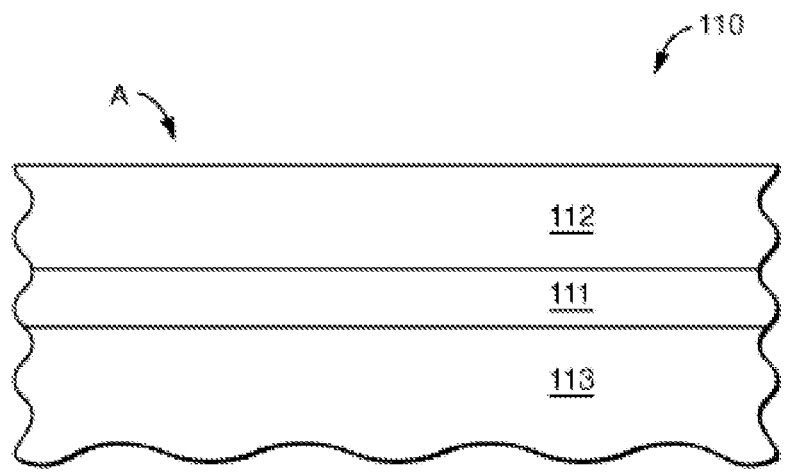
FIG. 4 is a cross-sectional detailed view of a portion of the stator of FIG. 2a, in the vicinity of the seal surface.

FIG. 4 is a cross-sectional detailed view of a small portion of the stator 110 in the vicinity of the contact surface A. The stator 110 includes a metallic substrate 113, a substantially smooth interlayer 111 on the substrate 113, and a substantially smooth low-friction surface layer 112 on the interlayer 111. The substrate is preferably formed of 316 stainless steel or titanium. The interlayer 111 is at least partially amorphous and is preferably selected to provide a good growth and adhesion layer for the surface layer 112. The interlayer 111 is preferably formed of substantially amorphous silicon dioxide, such as a glassy silica. The surface layer 112 is preferably formed of diamond-like carbon 112, with or without other components, such as hydrogen and/or silicon. For example, silicon is optionally included, of less than approximately 10 atomic %.

The layers 111 and 112 are deposited by any suitable deposition technique, including known techniques such as physical vapor deposition (PVD), plasma-assisted chemical vapor deposition (PACVD), ion beam deposition (IBD) or sputter deposition. For example, the interlayer 111 is formed of amorphous silica deposited by PACVD of tetraethoxysilane (TEOS) at 400° C.

The thickness of the interlayer 111 is preferably in a range of approximately 0.3 µm to approximately 0.5 µm, and the thickness of the surface layer 112 is preferably in a range of approximately 1.0 µm to approximately 3.0 µm. The interlayer 111 acts as a growth and adhesion substrate for the surface layer 112. The surface layer 112 is preferably a conformal deposit, which maintains a substantially smooth surface of the interlayer 111. No polishing is required to obtain a contact surface A having an average roughness (Ra) of approximately 0.025 µm or less (i.e., the average distance between a surface meanline and all points on the surface.)

Figure 5:
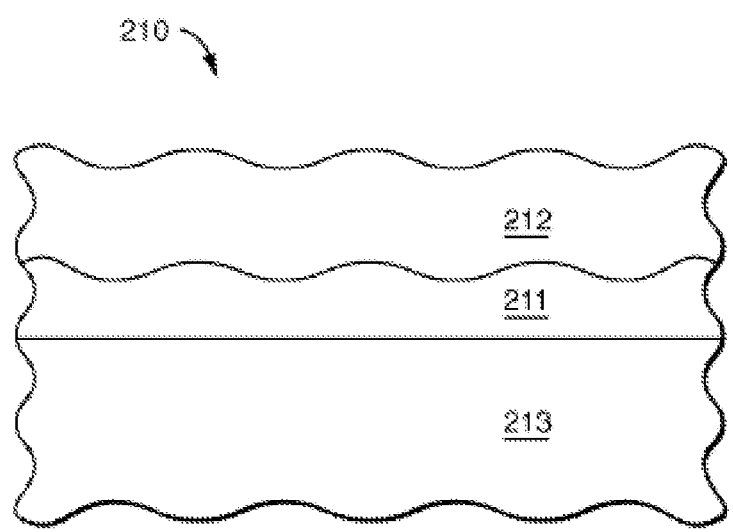
FIG. 5 is a cross-sectional detailed view of a small portion of a surface region of a prior art stator.

FIG. 5 is a cross-sectional detailed view of a small portion of a surface region of an example of a prior art stator 210, which entails greater fabrication complexity and/or contact-surface friction in comparison to the stator 110. The stator 210 includes a substrate 213 of stainless steel, a chromium layer 211 deposited on the substrate 210, and a diamond-like carbon layer 212 on the chromium layer. The layers 211 and 212 are deposited via PVD or PACVD. The thickness of the chromium layer 211 is approximately 0.4 µm, and the thickness of the diamond-like carbon layer 212 is approximately 2.0 µm.

After deposition of the diamond-like carbon layer 212, the surface of the stator 210 has nodules of approximately 0.5 µm to approximately 2.0 µm in diameter (parallel to the surface) and average vertical roughness (Ra) of approximately 0.05 µm to approximately 0.13 µm. Since such a roughness causes an undesirable level of friction, the as-deposited surface is typically mechanically polished to obtain an average roughness (Ra) of approximately 0.025 µm. The polishing process, however, typically introduces some surface damage.

Chromium typically exhibits columnar crystalline grow, leading to surface asperities. The surface roughness may lead to undesirable roughness of diamond-like carbon (DLC) or other material deposited on the chromium. Some features of the invention mitigate this problem. Thus, for example, where the stator 210, before polishing, may have a nodule surface density of approximately $2 \times 10^7/cm^2$ to $4 \times 10^8/cm^2$, the stator 110, without polishing, has a nodule surface density in a range of substantially no nodules to much less than $2 \times 10^7 cm^2$.

The valve 100 preferably has a coated metal-based stator 110 and a polymer-based rotor 120. The stator substrate 113 is formed of any suitable material, including metals, such as stainless steel, titanium and aluminum. The rotor 120 is preferably formed of a polymer material that is selected for its ability to form a liquid-tight seal at desired pressures. The polymer includes any suitable material, including known materials.

One of the suitable polymeric materials is polyether-ether-ketone, such as PEEK polymer (available from Victrex PLC, Lancashire, United Kingdom.) Alternative polymers include, for example, fluoropolymers such as polytetrafluorothylene (available as TEFLON polymer from Dupont Engineering Polymers, Newark, Del.), chlorotetrafluoroethylene, polychlorotrifluoroethylene (available as NEOFLON PCTFE fluoropolymer from Fluorotherm Polymers, Inc., Fairfield, N.J.), and modified copolymer fluoropolymers (for example, a modified copolymer of tetrafluoroethylene and ethylene available as DUPONT TEFZEL fluoropolymer, which is resistant to concentrated nitric acid or sulfuric acid), and other polymers, such as polyimide (available as DUPONT VESPEL polyimide.)

In some embodiments, the rotor 120 is formed of a composite material. For example, in some of these embodiments, the rotor 120 is formed of a mixture of a polymer, such as polyether-ether-ketone, and about 5% by weight of glass, fiberglass, carbon, and/or or other particles and/or fibers.

The rotor 120 optionally includes a mixture of polymers, such as a combination of polyetheretherketone and tetrafluoroethelene. An optional combination of polyetheretherketone and tetrafluoroethelene has 50% to 90% polyetheretherketone and 10% to 50% tetrafluoroethelene, or 60% to 80% polyetheretherketone and 20% to 40% tetrafluoroethelene.

The injector valve 100 is capable of hundreds of thousands of reliable rotation cycles, or more.

More generally, various embodiments of the invention include at least two contacting parts, at least one of which is formed at least in part of metal that is coated. The inventive features of the injector 100 are applicable to any suitable injector, including known injectors, for injecting a sample into a solvent flow.

Variations, modifications, and other implementations of what is described herein will occur to those of ordinary skill in the art without departing from the scope of the invention as described. For example, it will be apparent that the number and/or arrangement of various components of the above-described injector valve 100 are optionally modified, while still exploiting features of the invention. For example, alternative embodiments of the invention include other types of valves having sliding surfaces and applications in LC, such as vent valves, switching valves and diverter valves. Thus the terms "rotor" and "stator" are used herein to refer to components that slide against one another, in any of these embodiments. Accordingly, the invention is to be defined not by the preceding illustrative description but instead by the scope of the following claims.

What is claimed is:
1. A chromatography valve, comprising:
   a rotor comprising a rotor substrate; and
   a stator comprising a stator substrate, and having a contact surface in slidable contact with a contact surface of the rotor, wherein either or both the rotor and the stator further comprise a contact-surface coating comprising an at least partially amorphous interlayer adjacent to the contact surface, the interlayer comprising silica and having a thickness in a range of about 0.3 μm to about 0.5 μm, and a surface layer comprising diamond-like carbon on the interlayer, the surface layer having an unpolished contact surface, the unpolished contact surface having an average roughness (Ra) of approximately 0.025 μm or less.

2. The valve of claim 1, wherein the surface layer is substantially free of nodules.

3. The valve of claim 1, wherein the valve is a HPLC or higher-pressure rotary injector valve.

4. The valve of claim 1, wherein the interlayer is in direct contact with the substrate, and the surface layer is in direct contact with the interlayer.

5. The valve of claim 1, wherein the interlayer consists of substantially amorphous silica.

6. The valve of claim 1, wherein the interlayer is substantially free of a columnar-growth structure.

7. The valve of claim 1, wherein the stator substrate comprises steel or titanium.

8. The valve of claim 1, wherein the surface layer further comprises silicon in a concentration of less than about 10 atomic %.

9. The valve of claim 1, wherein the surface layer has a thickness in a range of about 1.0 μm to about 3.0 μm.

10. A method for making a chromatography valve, comprising:
providing a stator substrate defining a contact surface;
providing a rotor substrate defining a contact surface;
depositing an at least partially amorphous interlayer adjacent to the contact surface of either or both of the rotor substrate and the stator substrate, the interlayer comprising silica and having a thickness in a range of about 0.3 μm to about 0.5 μm;
depositing a surface layer comprising diamond-like carbon on the interlayer, the surface layer having an unpolished contact surface, the unpolished contact surface having an average roughness (Ra) of approximately 0.025 μm or less; and
disposing the contact surfaces in slidable contact.

11. The method of claim 10, wherein the interlayer substantially consists of silica.

12. The method of claim 10, wherein the interlayer is substantially amorphous.

13. The method of claim 10, wherein the surface layer has a thickness in a range of about 1.0 μm to about 3.0 μm.

* * * * *